(12) United States Patent
Hallett (10) Patent No.: US 11,166,714 B2
(45) Date of Patent: Nov. 9, 2021

(54) BRAIDED SUTURE COAT

(71) Applicant: Surgical Specialties Corporation, Braintree, MA (US)

(72) Inventor: Brian S. Hallett, Taunton (GB)

(73) Assignee: Surgical Specialties Corporation, Westwood, MA (US)

( * ) Notice: Subject to any disclaimer, the term of this patent is extended or adjusted under 35 U.S.C. 154(b) by 0 days.

(21) Appl. No.: 15/523,846

(22) PCT Filed: Nov. 4, 2015

(86) PCT No.: PCT/US2015/059081
§ 371 (c)(1),
(2) Date: May 2, 2017

(87) PCT Pub. No.: WO2016/073635
PCT Pub. Date: May 12, 2016

(65) Prior Publication Data
US 2017/0333038 A1    Nov. 23, 2017

Related U.S. Application Data

(60) Provisional application No. 62/075,090, filed on Nov. 4, 2014.

(51) Int. Cl.
*A61B 17/06* (2006.01)
*A61L 17/10* (2006.01)
(Continued)

(52) U.S. Cl.
CPC ........ *A61B 17/06166* (2013.01); *A61B 17/04* (2013.01); *A61B 17/06* (2013.01);
(Continued)

(58) Field of Classification Search
CPC .......... A61B 2017/06171; A61B 2017/06176; A61B 2017/0618; A61B 2017/06185;
(Continued)

(56) References Cited

U.S. PATENT DOCUMENTS 1,254,031 A    1/1918   Davis
2,576,576 A    11/1951  Cresswell et al.
(Continued)

FOREIGN PATENT DOCUMENTS

EP    1623726 A2    2/2006
EP    1847276 A1    10/2007
(Continued)

OTHER PUBLICATIONS

Extended European Search Report for EP 15856718.0, dated Jun. 15, 2018. 7 pages.
(Continued)

*Primary Examiner* — Katherine H Schwiker
(74) *Attorney, Agent, or Firm* — Seed Intellectual Property Law Group LLP (57) ABSTRACT

High-consistency nonabsorbable braided suture stock of specified size is prepared from twisted multifilament strands braided together with a tightness of weave of less than 60 picks/inch. The suture stock can be cut to provide sutures, which may be combined with needles to provide surgical sutures for wound closure.

9 Claims, 1 Drawing Sheet (51) Int. Cl.
*D04C 1/06* (2006.01)
*A61B 17/04* (2006.01)
*A61B 17/00* (2006.01)

(52) U.S. Cl.
CPC ............. *A61L 17/10* (2013.01); *A61L 17/105* (2013.01); *D04C 1/06* (2013.01); *A61B 2017/00526* (2013.01); *D10B 2321/0211* (2013.01); *D10B 2509/04* (2013.01)

(58) Field of Classification Search
CPC ............ A61B 2017/0619; A61B 17/04; A61B 17/06166; A61L 17/00; A61L 17/005; A61L 17/04; A61L 17/06; A61L 17/08; A61L 17/10; A61L 17/105; A61L 17/12; D10B 2321/0211
See application file for complete search history.

(56) References Cited

U.S. PATENT DOCUMENTS

| | | | |
|---|---|---|---|
| 2,734,506 A | 2/1956 | Nichols et al. | |
| 3,130,278 A | 4/1964 | Douchet | |
| 3,187,752 A * | 6/1965 | Glick | A61L 17/145 606/231 |
| 3,390,681 A | 7/1968 | Kurtz et al. | |
| 3,565,077 A | 2/1971 | Glick | |
| 3,572,343 A * | 3/1971 | Hirsch | A61L 17/04 606/228 |
| 3,942,532 A | 3/1976 | Hunter et al. | |
| 3,949,755 A | 4/1976 | Vauquois | |
| 4,043,344 A * | 8/1977 | Landi | A61L 17/145 606/230 |
| 4,047,533 A * | 9/1977 | Perciaccante | A61B 17/06166 606/230 |
| 4,105,034 A | 8/1978 | Shalaby et al. | |
| 4,510,934 A | 4/1985 | Batra | |
| 4,546,769 A * | 10/1985 | Planck | A61B 17/06166 606/231 |
| 4,790,850 A | 12/1988 | Dunn et al. | |
| 4,792,336 A | 12/1988 | Hlavacek et al. | |
| 4,946,467 A | 8/1990 | Ohi et al. | |
| 5,019,093 A | 5/1991 | Kaplan et al. | |
| 5,226,912 A | 7/1993 | Kaplan et al. | |
| 5,274,074 A | 12/1993 | Tang et al. | |
| 5,318,575 A | 6/1994 | Chesterfield et al. | |
| 5,456,722 A | 10/1995 | McLeod et al. | |
| 5,540,703 A | 7/1996 | Barker, Jr. et al. | |
| 5,628,756 A | 5/1997 | Barker, Jr. et al. | |
| 5,662,682 A | 9/1997 | Chesterfield et al. | |
| 5,984,933 A | 11/1999 | Yoon | |
| 6,045,571 A | 4/2000 | Hill et al. | |
| 6,203,564 B1 | 3/2001 | Hutton et al. | |
| 6,716,234 B2 | 4/2004 | Grafton et al. | |
| 8,088,146 B2 | 1/2012 | Wert et al. | |
| 8,632,566 B2 | 1/2014 | Olson | |
| 8,672,966 B2 | 3/2014 | Wert et al. | |
| 2003/0050666 A1 | 3/2003 | Grafton | |
| 2003/0050667 A1 | 3/2003 | Grafton et al. | |
| 2003/0139775 A1 | 7/2003 | Grafton | |
| 2004/0267313 A1 | 12/2004 | Amery et al. | |
| 2005/0033362 A1 | 2/2005 | Grafton | |
| 2005/0119696 A1 | 6/2005 | Walters et al. | |
| 2005/0125034 A1 | 6/2005 | Cichocki, Jr. | |
| 2005/0125036 A1 | 6/2005 | Roby | |
| 2005/0149118 A1 | 7/2005 | Koyfman et al. | |
| 2005/0277985 A1 * | 12/2005 | Wert | A61B 17/06166 606/228 |
| 2006/0025818 A1 | 2/2006 | Ferguson | |
| 2007/0135840 A1 | 6/2007 | Schmieding | |
| 2008/0009903 A1 | 1/2008 | Schmieding et al. | |
| 2008/0021501 A1 | 1/2008 | Schmieding | |
| 2009/0248071 A1 * | 10/2009 | Saint | A61B 17/0401 606/232 |
| 2010/0274282 A1 * | 10/2010 | Olson | A61L 17/04 606/228 |
| 2012/0101523 A1 | 4/2012 | Wert et al. | |
| 2013/0239539 A1 * | 9/2013 | Li | B60C 9/005 57/3 |
| 2013/0296934 A1 * | 11/2013 | Sengun | A61B 17/0401 606/232 |
| 2014/0025106 A1 | 1/2014 | Olson | |
| 2014/0052175 A1 | 2/2014 | Koyfman et al. | |

FOREIGN PATENT DOCUMENTS

| | | |
|---|---|---|
| EP | 2275148 A1 | 1/2011 |
| GB | 2081585 A | 2/1982 |
| RU | 108713 U1 | 9/2011 |
| WO | 1992/010137 A1 | 6/1992 |
| WO | 2008/091690 A1 | 7/2008 |

OTHER PUBLICATIONS

International Preliminary Report on Patentability for PCT/US2015/059081, dated May 9, 2017, 9 pages.
International Search Report and Written Opinion for PCT/US2015/059081, dated Jan. 27, 2016, 12 pages.
Dunn, David L., et al., "Wound Closure Manual," Ethicon, Inc., 127 pages, 2005.
Russian Search Report for application RU 2017119018, dated May 6, 2019, 4 pages.

* cited by examiner

BRAIDED SUTURE COAT

CROSS-REFERENCE TO RELATED APPLICATION

This application claims the benefit under 35 U.S.C. § 119(e) of U.S. Provisional Patent Application No. 62/075,090, filed Nov. 4, 2014, which application is hereby incorporated by reference in its entirety.

FIELD OF THE INVENTION

The present invention relates generally to braided elongate materials such as surgical sutures, and their manufacture.

BACKGROUND

Surgical sutures made from braided synthetic fibers have been described in many printed publications and are commercially successful products. Such sutures may be made from absorbable and/or nonabsorbable fibers. Also, such sutures may or may not have a central cavity that runs the length of the suture, and when such a cavity is present, that cavity may or may not be filed by a separate core material. When the central cavity is empty, the suture is sometimes referred to as a coreless suture.

Surgical sutures and other elongate medical products formed by fiber braiding are described in the following exemplary documents: U.S. Pat. Nos. 6,716,234; 6,203,564; 6,045,571; 5,984,933; 5,662,682; 5,628,756; 5,540,703; 5,456,722; 5,318,575; 5,274,074; 5,226,912; 5,019,093; 4,946,467; 4,792,336; 4,790,850; 4,546,769; 4,510,934; 4,047,533; 4,043,344; 3,949,755; 3,565,077; 3,130,278; US Publication Nos. (US) 2005/0149118; 2005/0125036; 2005/0125034; 2005/0119696; 2003/0139775; 2003/0050667; PCT Publication No. (WO) 92/10137; and Great Britain Patent No. 2081585.

Teleflex Medical OEM (Gurnee, Ill., USA) markets Force Fiber® suture, which is advertised to be a coreless braided suture available in sizes 5-0, 4-0, 3-0, 2-0, 0, 1, 2, 3/4 and 5. Force Fiber® suture is made from ultra-high molecular weight polyethylene (UHMWPE) and may incorporate polyester, polypropylene or nylon. See also U.S. Pat. Nos. 8,672,966 and 8,088,146, as well as European Publication Nos. EP 1623726 and EP 2275148.

CP Medical (Portland, Oreg., USA) markets Powerfiber™ (USP sizes 2 & 2/0 (metric sizes 5 & 3)) and CP Fiber (USP sizes 7-0 through 5 (metric sizes 0.5-7)) sutures. In addition to a braided sleeve made from UHMWPE, these sutures include a core made from polyester. CP Medical also markets Polybond® suture, which is a braided polyester nonabsorbable, sterile surgical suture, composed of polyethylene terephthalate. Polybond® suture is available in USP sizes 8-0 through 5 (metric sizes 0.4-7). See also U.S. Publication No. 2006/0025818

Arthrex (Naples, Fla., USA) markets FiberWire® suture, advertised to be constructed of a multi-strand, long chain ultra-high molecular weight polyethylene (UHMWPE) core with a braided jacket of polyester and UHMWPE. See also PCT Publication WO2008/091690 and US Patent Publication Nos. 2003/050666; 2007/135840; U52008/009903 and 2008/021501.

Conmed (Largo, Fla., USA) markets HiFi™ surgical suture, which is marketed as a braided, nonabsorbable ultra high molecular weight polyethylene suture indicated for soft tissue repair in orthopaedic procedures. This product contains Dyneema® Purity, which is a trademark of DSM Dyneema B. V. or an affiliate of Koninklijke DSM N.V. HiFi reportedly contains no central core. HiFi™ suture is available in USP sizes including 2, 5, 0 and 2-0.

Smith & Nephew (London, England) markets Ultrabraid™ suture. Ultrabraid™ suture is advertised as a high-strength polyethylene suture for attaching soft tissue to bone. Ultrabraid™ suture reportedly is made of an ultra-high molecular weight polyethylene fiber with a unique, proprietary braid configuration which allows it to slide through tissue and anchors easily, resist fraying and create a stronger knot than traditional suture. Ultrabraid™ suture reportedly does not contain a core.

The present disclosure provides an improved process for preparing braided medical products, e.g., braided sutures including braided surgical sutures for wound closure, as well as providing suture stock and sutures which may be prepared by this process.

SUMMARY

Briefly stated, the present disclosure provides a method of preparing braided stock, such as a braided suture stock, where the stock may be cut into desired lengths, e.g., to form surgical suture. In one embodiment, the method includes using multifilament fiber that has at least 150, and preferably at least 200 twists/meter. This highly twisted multifilament fiber may be braided into a coreless braid having 18-24 plaits/cm in order to prepare a suture stock.

In one embodiment, high-consistency nonabsorbable braided suture stock of specified size is prepared from twisted multifilament strands braided together with a tightness of weave of less than 60 picks/inch. The suture stock can be cut to provide sutures, which may be combined with needles to provide surgical sutures for wound closure.

The present disclosure also provides surgical suture stock, and surgical sutures, which may be made by the described process. For example, the present disclosure provides, in first and second aspects:

1) A surgical suture stock (first aspect) or a surgical suture cut therefrom (second aspect), comprising:
   a. an elongate tubular sleeve surrounding an elongate tubular cavity, the suture lacking a core;
   b. the sleeve comprising a plurality of multifilament strands braided together, the sleeve lacking any monofilament strands;
   c. the multifilament strand comprising a plurality of filaments, a filament comprising a plurality of polymer chains, where the polymer chains in at least some of the filaments are ultra-high molecular polyethylene (UHMWPE);
   d. multifilament strand has a twist of 150 to 250 turns per meter; and
   e. the strands in the sleeve are braided together at 8 to 24 plaits per centimeter.
2) The suture stock or suture of embodiment 1 including at least one marker strand.
3) The suture stock or suture of embodiment 1 where the strands in the sleeve are braided together at 9-23 plaits/centimeter, or at 10-22 plaits/centimeter; or at 11-21 plaits/centimeter; or at 12-20 plaits/centimeter; or at 13-19 plaits/centimeter; or at 14-18 plaits/centimeter.
4) The suture stock or suture of embodiments 1-3 wherein the multifilament comprises 20-100 filaments, or 30-60 filaments.

5) The suture stock or suture of embodiments 1-4 comprising 12-15 strands, or 16-19 strands, or 20-23 strands; or 24-27 strands; or 28-31 strands; or 32-35 strands.
6) The suture stock or suture of embodiments 1-5 wherein each strand is characterized by a denier value of 50-160; or by a denier value of 60-150; or by a denier value of 70-140; or by a denier value of 80-130; or by a denier value of 90-120; or by a denier value of 95-115; or by a denier value of 100-110.
7) The suture stock or suture of embodiments 1-6 wherein 90% or less of the strands in the suture are made from ultra-high molecular weight polyethylene; or wherein 80% or less of the strands in the suture are made from ultra-high molecular weight polyethylene; or wherein 70% or less of the strands in the suture are made from ultra-high molecular weight polyethylene; or wherein 60% or less of the strands in the suture are made from ultra-high molecular weight polyethylene; or wherein 50% or less of the strands in the suture are made from ultra-high molecular weight polyethylene.
8) The suture stock or suture of embodiments 1-7 comprising multifilament strands made from nylon.
9) The suture stock or suture of embodiments 1-7 comprising multifilament strands made from polypropylene.
10) The suture stock or suture of embodiments 1-7 comprising multifilament strands made from polyester.
11) The suture stock or sutures of embodiments 1-7 containing 11 strands of UHMWPE and 5 strands of nylon.
12) The suture stock or suture of embodiments 1-11 which is USP size 2.

As another example, the present disclosure provides:
13) A surgical suture comprising:
   a. an elongate tubular sleeve surrounding an elongate tubular cavity, the suture lacking a core;
   b. the sleeve comprising of a plurality of multifilament strands braided together, the sleeve lacking any monofilament strands;
   c. the multifilament strand consisting of a plurality of UHMWPE filaments and a plurality of nylon filaments, where a UHMWPE filament comprising a plurality of polymer chains that are ultra-high molecular polyethylene (UHMWPE) and where the nylon filaments comprise a plurality of polymer chains that are nylon, where;
   d. the filaments in the multifilament strand are twisted together at 8 to 24 plaits per centimeter;
   e. the strands in the sleeve are braided together at 150 to 350 turns per meter; and
   f. the suture is USP size 2.

As mentioned above, the present disclosure provides a method of making a surgical suture stock, where the stock can be cut to form surgical suture, the surgical suture stock comprising an elongate tubular sleeve surrounding an elongate tubular cavity, the suture stock lacking a core. In one embodiment, the method comprises braiding together a plurality of multifilament strands at 8-24 plaits per centimeter, where the multifilament strands consist of a plurality of UHMWPE filaments and a plurality of nylon filaments, where the UHMWPE filament comprises a plurality of polymer chains that are ultra-high molecular polyethylene (UHMWPE) and where the nylon filaments comprise a plurality of polymer chains that are nylon. Optionally, the multifilament strands have a twist of 150 to 350 turns per meter at the time that they are being braided. Optionally, 11 strands of UHMWPE and 5 strands of nylon are braided to form a USP size 2 suture stock and suture by this method. As another option, 12 strands of UHMWPE and 4 strands of nylon are braided to form a USP size 5 suture stock and suture by this method.

The details of these and other embodiments are set forth in the description below. The features illustrated or described in connection with one exemplary embodiment may be combined with the features of other embodiments. Other features, objects and advantages will be apparent from the description and the claims. In addition, the disclosures of all patents and patent applications referenced herein are incorporated by reference in their entirety.

BRIEF DESCRIPTION OF THE DRAWINGS

In the figures, identical reference numbers identify similar elements. The sizes and relative positions of elements in the figures are not necessarily drawn to scale and some of these elements are enlarged and positioned to improve figure legibility. Further, the particular shapes of the elements as drawn are not intended to convey any information regarding the actual shape of the particular elements, and have been solely selected for ease of recognition in the figures.

DETAILED DESCRIPTION OF THE INVENTION

In one aspect the present disclosure provides a surgical suture, and more specifically a braided surgical suture. In another aspect the present disclosure provides a process for making braided suture stock from which the surgical suture may be formed by cutting of the suture stock at appropriate locations. The present invention may be understood more readily by reference to the present detailed description and the Example(s) included herein.

It is to be understood that unless specifically defined to the contrary, the terminology used herein is to be given its traditional meaning as known in the relevant art. Any headings used within this document are only being utilized to expedite its review by the reader, and should not be construed as limiting the invention or claims in any manner. As used throughout this document, including the claims, the singular form "a", "an", and "the" include plural references unless indicated otherwise. For example, "a" braid includes one or more braids. As another example, "a" carrier braider refers to one or more carrier braiders.

An "end" refers to a handleable length of flexible elongate material which may be braided, e.g., fiber, filament, thread, yarn. In general, an end may be monofilament or multifilament, although the ends used to prepare the suture stock and sutures of the present invention are multifilament. A multifilament end may be twisted or otherwise constructed or treated so that its component filaments remain held together to form a unitary thread-like structure.

A "filament" refers to a synthetically produced monofil fiber as formed by means of a die orifice of a spinneret or a multiple-orifice spinneret. A "multifilament" strand or yarn refers to a bundle of filaments that are held together so as to provide an "end".

Yarn is a generic term for a continuous strand of textile fiber, filament or material in a form suitable for intertwining to form a textile structure via any one of a number of textile processes. The multifilament strands of the present disclosure are an example of a yarn.

In one aspect, the present disclosure provides a surgical suture comprising an elongate tubular sleeve surrounding an elongate tubular cavity. In one embodiment, the suture lacks a core. As mentioned previously, certain surgical sutures comprising an elongate tubular sleeve surrounding an elongate tubular cavity, both with and without a core, have been described in the patent literature and/or are currently materials of commerce. The components of such sutures are known by various names. For example, various alternative terms are used in the art to refer to a sleeve, e.g., cover, jacket and sheath. Likewise various alternative terms are used in the art to refer to the cavity, e.g., hole and opening. As the suture of the present disclosure lacks a central core, it may be said to be a coreless suture, i.e., a suture that has a space for a core to fit within, but where space is not occupied by a core material.

In one aspect, the present disclosure provides a surgical suture comprising a sleeve that is formed from materials including a plurality of multifilament strands, where the multifilament strands are braided together. In one embodiment, the sleeve lacks any monofilament strands. In general, multifilament strands are made by combining filaments, where filaments are drawn or spun from a polymer melt or gel. Strands may be made from any number of filaments, but typically for suture manufacture a suitable strand is made from 20-100 filaments, with 30-60 filament multifilament strands being very common.

In forming a strand, a selected number of filaments are brought together to form a multifilament strand. In one common practice, those filaments are formed by pulling material from a polymeric melt or gel, where the pulled material cools as it exits the melt or gel, and thereupon forms a filament. When a multifilament strand is the manufacturing objective, then a plurality of filaments are pulled from the melt or gel in very close proximity to one another, and after the filaments are cooled they are brought together, or in other words bundled together, into a single strand composed of a plurality of filaments.

In order to keep those filaments together so that the strand has a unitary thread-like appearance and feel, various techniques may be used. In one technique, known as heat-set, the bundled multifilament strand is heated to provide for a sintering effect between the filaments, i.e., the filaments are heated to near their softening point and then held together during cooling, whereupon portions of the outer surface of a filament will stick to portions of the outer surface of neighboring filaments, to provide for a co-joined structure. Chemical treatment is also known to be able to achieve an effectively integral strand from a plurality of filaments.

Twisting may be used to convert a plurality of filaments into a multifilament strand. In a twisting process, the plurality of recently formed filaments are rotated as they exit the filament forming apparatus and are thereby bundled and held together. The filaments may be twisted in either a clockwise or counterclockwise manner. A convention for describing the direction of twist begins by holding the yarn in a vertical position. If the spirals conform to the direction of the slope of the central part of the letter S, the yarn has an S twist; if they conform to the slope of the letter Z, the yarn has a Z twist. In either case, the filaments that form the outer surface and the near-outer-surface of the multifilament strand will take on a spiral shape, effectively encircling the filaments that comprise the interior of the multifilament strand. With this twisting, the filaments are held closely together. Absent this twisting, or some other process/treatment, the individual filaments tend to separate from one another.

The extent of twisting may be measured by known instrumentation. For example, James H. Heal & Co., Ltd. (Halifax, England) manufactures and sells a machine that measures the twist of the strand. Alternatively, an electronic twist tester may be used to determine the twist of twisted (S&Z) yarns, where the tester is able to evaluate twist by any of three methods: traditional method (untwisting, retwisting of single yarns), direct method (untwisting for plied yarns, threads and multi-filaments) and "Schutz" method (untwisting, retwisting and double counter-check for OE). Dowell Science and Technology Co., Ltd. (Hong Kong, China) manufactures and sells such an electronic twist tester as their Automatic Yarn Twisting Tester Y331A-III). Mesdan Lab (Brescia, Italy) also offers a suitable instrument that can be used to measure the twist of a multifilament fiber. Twisting can also be measured through careful visual inspection.

Sometimes, a manufacturer of multifilament strand imparts a small amount of twist to a multifilament strand in order to keep the filaments together. This small twist is enough to ensure that the filaments remain together during transport and use. This small twist, which may be referred to as a manufacturer's twist, is typically in the range of 80-140 turns/meter, and is often about 120 turns/meter which corresponds to about 3 turns/inch. A manufacturer's twist of this degree is adequate to keep the plurality of filaments together in a multifilament form.

The present disclosure provides a suture and process that incorporates/utilizes multifilament strands that have a greater degree of twist than typically afforded by multifilament strand manufacturers, and accordingly provides surgical sutures incorporating such highly twisted multifilament strands.

The twist of the multifilament strand as used herein, and as reported in terms of turns/meter (tpm), is, in various embodiments, greater than 150, or greater than 160, or greater than 170, or greater than 180, or greater than 190, or greater than 200, or greater than 210, or greater than 220, or greater than 230, or greater than 240, or greater than 250, or greater than 260, or greater than 270, or greater than 280, or greater than 290, or greater than 300, or greater than 310, or greater than 320, or greater than 330, or greater than 340, or greater than 350, or greater than 360, or greater than 370, or greater than 380, or greater than 390. As for an upper value, it is observed that the benefits of the present invention are observed at twists of less than 400 (again, as measured in terms of turns/meter), or less than 390, or less than 380, or less than 370, or less than 360, or less than 350, or less than 340, or less than 330, or less than 320, or less than 310. For example, suitable ranges are 150 to 350, or 160 to 340, or 180 to 320, or 200 to 300 turns/meter.

The enhanced twist of the multifilament strands used in making the suture stock of the present disclosure may be transitory in the sense that no chemical or thermal means are necessarily employed to permanently maintain the enhanced twist over time and with handling. Accordingly, the highly twisted strands of the present disclosure may, in one embodiment, be used promptly after they are given the enhanced twist, where promptly means within hours of twisting. If the highly twisted strands are not used promptly, then in one embodiment they are handled to a minimal extent prior to braiding so that they do not lose their enhanced twist, or at least they do not lose too much of the enhanced twist so that the benefits of the enhanced twisting are not realized. In one embodiment, the twist of the multifilament strand is enhanced (compared to a manufacturer's twist) to at least 150 tpm or other enhanced twist value as set forth herein, and then this fiber having an enhanced twist is used to form a suture stock. In one embodiment, the present disclosure provides suture stock comprising multifilament fiber with an enhanced twist. In another embodiment, the present disclosure provides suture comprising multifilament fiber with an enhanced twist. In one embodiment, the braiding processes of the present disclosure utilize a multifilament fiber which has undergone a process that imparted an enhanced twist to the fiber of at least 150 tpm, or other enhanced value as set forth herein.

As mentioned previously, in one embodiment neither the sleeve nor the suture contains a monofilament strand. In general, in order for a monofilament strand to make a noticeable contribution to either the appearance of the suture or to the physical properties of the suture, the monofilament strand will need to be of a significant diameter. The present inventors have found that such monofilaments (i.e., those having a significant diameter) tend to impart undesirable stiffness to the suture, and accordingly the sutures of the present disclosure may optionally not include any monofilament strand(s).

As mentioned previously, the present disclosure provides a surgical suture comprising a sleeve that is formed from materials including a plurality of multifilament strands, where the multifilament strands are braided together to form the sleeve. The use of braiding to form any of sutures, cores for sutures, and sleeves for sutures, is well known in the art and is commonly accomplished using a machine called a carrier braider. Many companies worldwide make and/or sell carrier braiders suitable for the manufacture of sutures of the present disclosure, including Cobra (Congleton, Cheshire, England), OMA S.r.l. (Milan, Italy), August Herzog Maschinenfabrik GmbH & Co. KG (Oldenburg, German&; Suman Technologies (Karnataka, India) and Xuzhou Henghui Braiding Machine Co., Ltd. (Jiangsu, China). Suitable braider carriers manufactured J.B. Hyde & Co., Ltd, England, are available on the resale market.

Likewise, the operation of braider carriers to form certain sutures is well known in the art. In general, braider carriers are designed to carry a maximum number of bobbins of strands, called packages, of either monofilament or multifilament strands. Braider carriers that carry a maximum of 8, 12, 16, 20, 24, 28 and 32 packages (also referred to as spools) are commercially available. It is common, but not necessary, to place packages in each available location on the carrier braider, when setting up the machine to produce a braid. When making a core-containing suture, a length of core is held in the middle of the braider carrier, and the filaments from each package are braided together around that core—like a maypole is braided. When making a coreless suture, that core is omitted but the process is otherwise essentially the same. If the core is omitted, then the elongate hollow tubular cavity which forms within the center of the braided sleeve is typically circular or near-circular in cross section. If an elongate tubular cavity having a non-circular cross-section is desired, then a mandrel of any desired cross-section may be placed in the middle of the carrier, and the sleeve is braided around that mandrel so that the cavity essentially adopts the cross-sectional shape and size of the mandrel. In this manner, the sutures of the present disclosure may have, and in optional embodiments do have, a wide variety of cross-sectional shapes, including circular, triangular, square, and rectangular.

The present disclosure provides a surgical suture comprising a sleeve that is formed from materials including a plurality of multifilament strands. A multifilament strand comprises a plurality of filaments, where a filament comprises a plurality of polymer chains. In the ordinary course, a multifilament manufacturer produces a plurality of identical filaments, and then bundles those identical filaments into a multifilament strand. Thus, each filament is formed from essentially identical polymer chains, and each multifilament fiber is formed from essentially identical filaments.

The surgical sutures of the present disclosure may be prepared from any suitable polymer or mixture of polymers. In one embodiment, the sutures are prepared from a mixture of polymers, e.g., the braid is formed from strands made from polymer "A" and strands made from polymer "B". In one embodiment, the suture is prepared from a plurality of nonabsorbable strands, e.g., polyolefin. In one embodiment, the suture incorporates multifilament made from ultra-high molecular weight polyethylene (UHMWPE). In various embodiments, not all of the strands are made from UHMWPE. For example, and based on the total number of strands used to form the sleeve, the strands made from UHMWPE may constitute less than 95%, or less than 90%, or less than 85%, or less than 80%, or less than 75%, or less than 70%, or less than 65%, or less than 60%, or less than 55%, or less than 50% of the number of strands. As for a minimum number of UHMWPE strands, in various embodiments the sleeve contains at least 25%, or at least 30%, or at least 35%, or at least 40%, or at least 45%, or at least 50%, or at least 55%, or at least 60%, or at least 65%, or at least 70%, or at least 75%, or at least 80% UHMWPE multifilament strands. Suitable exemplary ranges include 50-75% of the strands used to form the suture stock are made from UHMWPE, or 50-70% of the strands are made from UHMWPE.

When a suture is formed from a mixture of polymers, e.g., from UHMWPE and a second polymer, the second polymer may be any suitable polymer known for making sutures. In one embodiment, this second polymer is polyamide 6,6, also known as nylon. The present disclosure therefore provides, in one embodiment, sutures having an UHMWPE content as provided above, with the remainder of the content being provided by multifilament nylon strands.

When a suture is made from a mixture of polymers, e.g., from UHMWPE and a second polymer, the second polymer may be any suitable polymer known for making sutures. In one embodiment, this second polymer is polyester. The present disclosure therefore provides, in one embodiment, sutures having an UHMWPE content as provided above, with the remainder of the content being provided by multifilament polyester strands.

When a suture is made from a mixture of polymers, e.g., from UHMWPE and a second polymer, the second polymer may be any suitable polymer known for making sutures. In one embodiment, this second polymer is polypropylene. The present disclosure therefore provides, in one embodiment, sutures having an UHMWPE content as provided above, with the remainder of the content being provided by multifilament polypropylene strands.

In one embodiment, the polymer that is used to form a filament, and hence form the multifilament strand, may be selected from either ultra-high molecular polyethylene (also referred to as UHMWPE) or polyamide 6,6 (also referred to as nylon). Ordinarily, the multifilament strand will be formed from either UHMWPE or nylon, however it is possible to combine nylon filaments with UHMWPE filaments to form a hybrid multifilament strand, sometimes referred to as a heterologous strand. These ultra-high-molecular-weight polyethylene molecules are several orders of magnitude longer than those of high-density polyethylene (HDPE) due to a synthesis process that uses metallocene catalysis. UHMWPE molecules typically having 100,000 to 250,000 monomer units per molecule compared to HDPE which has on the order of 700 to 1,800 monomers per polymer chain. The UHMWPE filaments and multifilaments may be prepared by a process known as gel spinning, wherein a heated gel of UHMWPE is extruded through a spinneret. The extrudate is drawn through the air and then cooled in a water bath. The end-result is a fiber with a high degree of molecular orientation, and therefore exceptional tensile strength.

Multifilament strands formed from UHMWPE are commercially available. For example, suitable UHMWPE multifilament strands are commercially available from the DSM company (DSM Biomedical group, Exton, Pa., USA), which markets their Dyneema™ UHMWPE fibers, and the Honeywell company (Advanced Fibers and Composites group, Colonial Heights, Va., USA), which markets their Spectra™ UHMWPE fibers. The production of UHMWPE is described in, e.g., U.S. Pat. No. 4,413,110. Likewise, multifilament strands formed from nylon are commercially available. For example, suitable nylon strands are commercially available from Monosuisse AG (Emmenbrucke, Switzerland).

The present disclosure provides a surgical suture comprising a sleeve that is formed from materials including a plurality of highly twisted (e.g., 200 to 300 turns/meter) multifilament strands that have been braided together. During the braiding process, the operator of the carrier braider will select braiding conditions that impact the tightness of the weave. A braid can have a very tight weave such that the component strands are held fast against one another so that they can hardly move, or at the other end of the spectrum the braid can have a very loose weave such that the component strands are held only roughly in place and can readily slide past one another. The tightness of the weave can be, and commonly is, expressed in a numerical fashion, by reference to plaits per inch (or cm) or pics (sometimes spelled picks) per inch (or cm), where those terms are used interchangeably in the art.

Thus, in describing a braid it may be defined, in part, by the number of picks (or pics) per inch (or cm), according to conventional fashion. A "pick" is defined as the crossing of one strand over another, with the number of picks counted across the longitudinal axis. The greater the number of picks per inch, the tighter the weave of the braid. Also, as the picks per inch increase, more strands are consumed in manufacturing each inch of braid. It therefore typically takes a longer time to weave a braid having a relatively higher picks/inch, all other factors being equal. Also, a braid with a relatively high picks/inch will generally be more rigid and less pliable.

In a cover braid there are normally 12, 16, 20, 24, or 32 strands. Strands that revolve to the right may be referred to as "Z" strands, while strands that revolve to the left may be referred to as "5" strands. In a braided sleeve as provided herein, the pick count may be determined by looking at the number of strands rotating in one direction in one cycle length divided by the cycle length. Stated another way, pick count is expressed in picks per inch of length (PPI), which represents the number of times a particular strand crosses for every inch of braid length.

The degree of braid in the sleeve of the present disclosure comprising multifilament strand is reported in terms of plaits per centimeter of braid (or pics per centimeter), in either case abbreviated ppc, and in various embodiments is greater than 6 or greater than 7, or greater than 8, or greater than 9, or greater than 10, or greater than 11, or greater than 12, or greater than 13, or greater than 14, or greater than 15, or greater than 16, or greater than 17, or greater than 18, or greater than 19, or greater than 20, or greater than 21, or greater than 22, or greater than 23, or greater than 24, or greater than 25, or greater than 26, or greater than 27, or greater than 28, or greater than 29. As for an upper value, it is observed that the benefits of the present invention result with braids characterized by a pics/cm of, in various embodiments, less than 30, or less than 29, or less than 28, or less than 27, or less than 26, or less than 25, or less than 24, or less than 23, or less than 22, or less than 21, or less than 20, or less than 19, or less than 18, or less than 17, or less than 16, or less than 15. For example, suitable ranges are 10 to 24, or 10 to 22, or 10 to 20, or 10 to 18, or 10 to 17, or 10 to 16, or 11 to 24, or 11 to 22, or 11 to 20, or 11 to 18, or 11 to 17, or 11 to 16, or 12 to 24, or 12 to 22, or 12 to 20, or 12 to 18, or 12 to 17, or 12 to 16, or 13 to 24, or 13 to 22, or 13 to 20, or 13 to 18, or 13 to 17, as measured in terms of turns per centimeter.

The strands will be braided together at a constant plaits per inch, abbreviated ppi. Plaits per inch is equivalently referred to in the art as pics per inch, and is sometimes referred to as pic count. In various embodiments, the ppi will have a lower limit of 20, or 25, or 30, or 35, or 40, and will have an upper limit of 60, or 55, or 50, or 45. For example, the ppi may range from 20 to 60, or from 30 to 50, or from 35 to 45.

Whether in terms of inches or centimeters, plaits per distance is typically measured by eye with the assistance of a magnifying glass. Magnifying glasses may be incorporated into small devices through which the braided suture is passed while being evaluated for pic count. Carton produces a Scale Loupe 10× suitable for this purpose (Carton Optical Industries, Ltd., Tokyo, Japan).

In one embodiment, the present disclosure provides a nonabsorbable surgical suture of a specified size. Suture size as used herein follows the convention established in the United States Pharmacopeia (USP), which is sometimes referred to as the USP-NF. Thus, a nonabsorbable suture size of USP 0 has an average diameter within the range of 0.35 to 0.399 mm; a suture size of USP 1 has an average diameter within the range of 0.40 to 0.499 mm; a suture size of USP 2 has an average diameter within the range of 0.50 to 0.599 mm; a suture size of USP 3 and 4 has an average diameter within the range of 0.60 to 0.699 mm; a suture size of USP 5 has an average diameter within the range of 0.70 to 0.799 mm; a suture size of USP 6 has an average diameter within the ranges of 0.80 to 0.899 mm, a suture size of USP 7 has an average diameter within the range of 0.90 to 0.999 mm; a suture size of USP 8 has an average diameter within the range of 1.00 to 1.099 mm; a suture size of USP 9 has an average diameter of 1.100 to 1.199 mm; and a suture of size USP 10 has an average diameter of 1.200 to 1.299.

The size of a surgical suture may be measured by an instrument designed for the purpose of measuring suture size. Such an instrument may be called a diameter testing machine. One such instrument is the Milimar 01 made by Mahr GmbH (Mahr Federal Inc., Goettingen, Germany). Somewhere between 10 and 20 measurements of diameter are typically taken, and those values are averaged to provide the surgical suture size.

The present disclosure also provides for nonabsorbable sutures having a USP size of less than 0. For example, the suture or suture stock may be size 2-0, corresponding to an average diameter of 0.30 to 0.339 mm; or a size 3-0, corresponding to an average diameter of 0.20 to 0.249 mm, or a size 4-0, corresponding to an average diameter of 0.15 to 0.199 mm, or a size 5-0, corresponding to an average diameter of 0.1 to 0.149 mm, or may be of even smaller size.

Figure 1A:
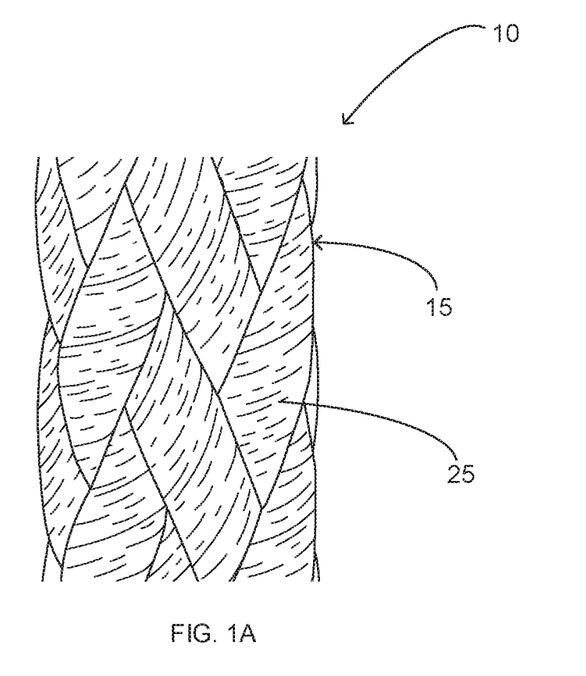
FIG. 1A is a side view of a surgical suture according to some embodiments.
Figure 1B:
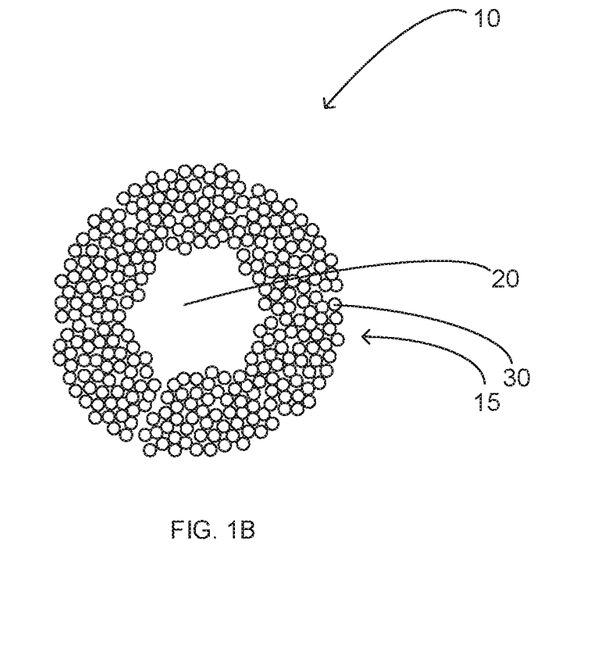
FIG. 1B is a corresponding cross-sectional view of the same.

An illustration of a surgical suture is shown in FIG. 1A and FIG. 1B. As shown, the surgical suture 10 comprises an elongate tubular sleeve 15 surrounding an elongate tubular cavity 20. The sleeve 15 comprises a plurality of multifilament strands 25 braided together. Each multifilament strand comprises a plurality of filaments 30 that are twisted together.

Suture is typically prepared by cutting a desired length of material from a longer length of material called suture stock. Suture stock is typically on the order of tens or hundreds of meters wound around a spool. Suture stock is the product prepared on a carrier braider. Thus, as the carrier braids multifilament into a sleeve form, this sleeve form is suture stock. To form the actual suture, a portion of suture stock having a desired length, e.g., 1 m or 100 cm, is cut from the stock. The suture properties described above, and the methods of making the sutures as described above, also apply to the properties and manufacturing process of suture stock.

A consistent uniform diameter is a required feature of a commercially successful suture. In order to provide a high yield of commercially acceptable suture, the suture stock must also demonstrate a consistent uniform diameter along its length. If the suture stock has locations where the diameter is not within the range specified by the USP for the suture being prepared, then those locations effectively form waste material. The present disclosure provides for a suture stock with a high level of diameter consistency along its length.

More specifically, it has been observed that the braiding of multifilament fibers to form a suture stock may result in instances where the diameter of the suture stock bulges out well beyond the desired diameter which is characteristic of the neighboring suture stock. The cause for this non-uniformity is not clear. It is speculated that during the braiding process, which necessarily places some additional stress on the multifilament strands and on the resultant braid, perhaps some of the component fibers of a multifilament strand break and then wind around or become entangled with itself or with the neighboring filaments, sometimes even extending to winding around and/or becoming entangled with the neighboring strands. Such an irregular event may lead to locations along the suture stock where the filaments bunch up to create a bulge or nodule, leading to a location on the suture stock which has a diameter well outside the desired range. The process of the present disclosure, wherein multifilament strands are twisted to degrees described herein, and then braided at a rate and weave density that provides the pics/inch described herein, provides a suture stock with an improved extent of diameter uniformity, as measured by a reduced number of locations where bulges or nodules are present in the suture stock. This process also provides a suture stock that can be cut to form sutures having desirable properties in terms of strength, pliability and knot strength, etc.

Thus, the present inventor has discovered that a relationship exists between the size of the suture, e.g., the suture size as characterized by the U.S. Pharmacopeia, the tightness of the weave, commonly expressed as ppi (plaits (or pics) per inch) and the twist of the multifilament strand, commonly expressed as tpm (turns per meter). Proper selection of these parameters results in a more efficient manufacturing process, i.e., a manufacturing process that provides a higher consistency of the desired product. The suture of the present disclosure is the result of this efficient manufacturing process. Suture thread cut from suture stock made according to the present disclosure has fewer incidents of being out-of-spec, so that less waste is created.

As the degree of twisting of the filaments in a multifilament strand is increased, an increased amount of stress is placed on the filaments, providing some undesirable weakening of the strand. As the degree of twisting of the filaments in a multifilament strand is decreased, there is a reduced tendency for the multiple filaments to stay together, and there is an increasing occurrence of the production of off-spec material. As the density of plaiting of the strands into a weave is increased, the resulting sleeve becomes more rigid, i.e., less flexible, and actually becomes weaker, i.e., more prone to break, due to the stress placed on the strands in order to create the high density weave. As the density of the plaiting is decreased, the resulting sleeve will lose bulk and the suture will not retain its USP size characterization. The present disclosure provides processes including suitable ranges of multifilament twisting and braid plait density for certain sizes of suture such that the production of off-spec material is greatly reduced while the properties of the multifilament strand are not unduly compromised and the size requirement of the suture is met.

For example, when preparing a suture having USP size of 1-4, e.g., USP size 2, the present disclosure provides a process that uses, and provides a corresponding surgical suture stock that has, multifilament strand where the constituent filaments are twisted together at 150-350 turns per meter, and those strands are braided into the form of a sleeve having 8-24 plaits per centimeter. Optionally, for a USP size 1-4 suture, the constituent filaments are twisted together at 170-330 turns per meter, and those strands are braided into the form of a sleeve having 9-23 plaits per centimeter, or 11-19 plaits/centimeter. As another option, for a USP size 1-4 suture, the constituent filaments are twisted together at 190-310 turns per meter, and those strands are braided into the form of a sleeve having 9-23 plaits per centimeter, or 11-19 plaits/centimeter, or 12 to 16 plaits/centimeter.

The present disclosure provides a process that braids multifilament strands that have a greater degree of twist than is typically afforded by multifilament strand manufacturers, and accordingly provides surgical suture stock incorporating such highly twisted multifilament strands.

A coating may be placed on the multifilament strand in order to provide a braided suture having improved tying and knot characteristics (see, e.g., U.S. Pat. No. 4,105,034 (poly(alkylene oxalate coating); U.S. Pat. No. 3,942,532 (aliphatic polyester coating); U.S. Pat. No. 3,390,681 (polytetrafluoroethylene coating); U.S. Pat. No. 3,187,752 (silicone coatings); U.S. Pat. No. 2,734,506 (polyacrylate coatings)); and/or to enhance the smooth passage of the suture through tissue, sometimes referred to as glide (see, e.g., U.S. Pat. No. 4,043,344 (discloses the use of polyoxyethylene-polyoxypropylene copolymer as a suture lubricant); U.S. Pat. No. 2,576,576 (lecithin may be used as a lubricating film); and U.S. Pat. No. 1,254,031 (discloses collagen coatings to provide a smooth uniform coating on an otherwise rough suture)) and/or to reduce bacterial infection of the suture. Compared to monofilament sutures, a braided suture has a greater risk of promoting infection due to capillarity, as the interstices between the filaments and strands can facilitate the spread of pathogens along the fiber. Triclosan is an exemplary antibacterial agent that may be coated onto a braided suture.

The strands may be of various colors. For example, a strand may be a natural color, i.e., no dye or pigment is added to the strand. A natural color is typically white. A strand may be dyed or manufactured to include pigment.

Strands of various colors are commercially available, including black, green, blue and red. The sutures and suture stock of the present disclosure may include two or more colors. For example, the suture may be prepared primarily from natural colored strands, with one or two colored strands being added. These colored strands are sometimes referred to as markers.

Strand manufacturers will impart a sufficient twist to a strand in order to keep the filaments together. Such a twist, which may be referred to as the manufacturer's twist, is typically on the order of 3 turns per inch. According to the present disclosure, additional twisting is imparted to the strand, above and beyond the twisting that is necessary to keep the filaments together. The present disclosure utilizes a strand having, in various embodiments, a twist value of greater than 3.5 turns per inch, or greater than 4 turns per inch, or greater than 4.5 turns per inch, or greater than 5 turns per inch, or greater than 5.5 turns per inch. The strand will typically have, in various embodiments, a maximum turn per inch of 7, or 6.5, or 6, or 5.5. For example, the twist of the strands utilized in making the suture stock of the present disclosure may be in the range of 4 to 6 turns per inch.

A common characterization of yarns, which may be used to characterize the multifilament strands of the present disclosure, is the linear density of the yarn. The linear density of a yarn is sometimes referred to as the count of a yarn. The count of a yarn is commonly reported in units of tex or denier. As a rough approximation, denier (or tex) is often used in the art to denote the thickness of a strand. For example, a strand of 100 denier is roughly twice as thick in diameter as is a strand of 50 denier, all other features of the strand being equal. It is worth emphasizing that equating denier and thickness is really only appropriate when comparing two fibers that are otherwise identical.

More precisely, the count (or linear density) of yarns may be characterized by providing the weight of some arbitrarily defined (but standard and specified in the art) length of strand, or by providing the length by which a defined weight of yarn may be extended. Over time, many different conventions have been adopted to describe linear density. Today, denier and tex are arguably the two most commonly employed conventions, where denier is the English system equivalent of the tex, where tex (or dtex) is commonly used in the metric system. Tex refers to the mass of yarn (as measured in grams) that is found in 1,000 meters of yarn. Dtex refers to the mass of yarn (as measured in grams) that is found in 10,000 meters of yarn. Denier refers to the mass of yarn as reported in grams for a length of 9000 meters. The denier is based on a natural reference: a single strand of silk is approximately one denier; a 9000-meter strand of silk weighs about one gram. To give some perspective, a typical human hair is on the order of 20 denier.

Spooling out 10,000 meters of yarn and then weighing the result is inconvenient. More conveniently, dtex may be determined by measuring out 10 meters of the yarn, compacting that length of yarn into the shape of a ball, and then weighing the ball on a scale that reports weight in terms of milligrams. The weight in milligrams will equal the count of the yarn in the deciTex (dTex) units.

A more highly twisted yarn (or multifilament) will tend to have a higher density per unit length, and accordingly the denier value of a multifilament strand will somewhat increase as the degree of twist in the multifilament strand increases.

The denier of the strands, as well as the number of strands used to form the braid, must each be selected appropriately in order to provide a suture having a desired USP size. Some amount of trial and error may be necessary. A hollow braid of USP size 2 may be prepared according to the present disclosure from 16 strands each of 100 denier, where the denier value is measured on a strand having a manufacturer's twist of about 120 turns/meter, i.e., prior to imparting an enhanced twist to the multifilament strand according to the present disclosure. Such a braid is conveniently prepared on a 16 carrier braider. Alternatively, one may employ fewer strands, each of a higher denier value, or more strands, each of a lower denier value. For instance, one may be prepare a hollow braid USP size 2 suture according to the present disclosure from 12 strands each of 150 denier.

To some extent, whether a specified number of strands having a specified denier value provides a USP 2 suture (or any other size suture) will depend on the tightness of the weave that forms the braid, as measured in pics per inch (or equivalently as measured in pics per centimeter). In one embodiment, the present disclosure sets the multifilament twist at about 200-300 turns/meter, and the braid weave at about 12-18 pics/centimeter, adjusts the number of braids and the denier of the strands to provide the required size of suture. The capacity of the carrier braider (i.e., whether it is, for example, an 8 carrier braider or a 12 carrier braider, etc.) used to form the suture is selected based on the number of strands that will be used to form the suture, keeping in mind that not all of the positions on a carrier braider need to be occupied by a spool of multifilament strand, but that a carrier braider of a given size can hold no more spools than there are carriers.

In one embodiment of the present disclosure, the suture stock and suture made therefrom is prepared from a blend of nylon strands and ultra-high molecular weight polyethylene (UHMWPE) strands. The nylon strand is made entirely from nylon filaments, where a nylon filament is made entirely or substantially from nylon, also known as polyamide 6,6. Likewise, the UHMWPE strands are made entirely from UHMWPE filaments, where a UHMWPE filament is made entirely or substantially from UHMWPE. The suture could be prepared from strands that were made from a blend of nylon filaments and UHMWPE filaments, however such strands are difficult to obtain from commercial strand suppliers and for that reason are not preferred for use in the present disclosure.

Thus, in one aspect the present disclosure provides a surgical suture of size USP 2 comprising a hollow braided tube and lacking a core, the braided tube being formed from components comprising a plurality of strands, the strands being braided together at a plait per inch of between 30 and 50, where less than 75% of the strands are UHMEPE strands and greater than 25% of the strands are nylon strands, the strands having a twist of between 3.5 and 6. The number of strands and the denier of each strand are selected so as to provide the desired size of suture. For example, the suture may be prepared from a total of 16 strands, where 11 strands are UHMWPE strands and 5 strands are nylon strands, and each strand is about 100 denier. Alternatively, the suture may be prepared from 12 strands, where 8 strands are UHMWPE and 4 strands are nylon strands, and each strand is about 150 denier. Based on the teachings herein, the skilled person may prepare surgical suture stock and surgical sutures, comprising a hollow braided tube and lacking a core, the braided tube being formed from components comprising a plurality of strands, in any desired suture size.

The following Examples are exemplary only, and thus non-limiting of the present disclosure.

EXAMPLES

Example 1

USP 2 Suture

A sixteen carrier braiding machine from Hyde was used to prepare a braided suture using 11 ends of UHMWPE fiber and 5 ends of nylon fiber. Of the sixteen carriers, eight carriers went to the left and eight carriers went to the right. Eight spools (also referred to as packages) of UHMWPE went to the right, while three spools of UHMWPE and five spools of nylon when to the left. Of the five nylon packages, three were blue and two were natural. The three colored strands were behind one another on the braid to give a chevron effect. No core was used. The nylon was first quality, raw white, high tenacity (68.0 cN/tex) dtex 110 (100 denier). The UHMWPE was likewise 100 denier. Before being braided, the nylon strands were twisted to 300 turns/meter while the UHMWPE strands were twisted to 200 turns/meter. Using a 22/68 gear ratio with a 65 mm haul-off on a Hyde braider carrier, a braid of 43 plaits per inch (17 plaits per centimeter) was obtained. The braid was captured or loaded onto a top bobbin. The total denier of the suture stock was 1816. Based on taking an average of several measurements: the knot pull was 13.4 kg; the break load was 27.4 kg; the break load % was 15.3. The average diameter was 0.533 which corresponds to USP size 2.

Example 2

USP 5 (ep7) Suture

A sixteen carrier braiding machine from Hyde was used to prepare a braided suture using 12 ends of UHMWPE fiber and 4 ends of nylon fiber. Of the sixteen carriers, eight carriers went to the left and eight carriers went to the right. Eight spools (also referred to as packages) of UHMWPE went to the right, while four spools of UHMWPE and four spools of nylon when to the left. Of the four nylon packages, two were blue and two were natural. The two colored strands were behind one another on the braid to give a chevron effect. No core was used. The nylon was first quality, raw white (except when dyed blue), high tenacity of about 100 denier (about (68.0 cN/tex) dtex 110). The UHMWPE was likewise about 100 denier. Before being braided, the nylon strands were twisted to 300 turns/meter while the UHMWPE strands were twisted to 200 turns/meter. Using a 30/60 gear ratio with a 50 mm haul-off on a Hyde braider carrier, a braid of 37 plaits per inch (14.5 plaits per centimeter) was obtained. The braid was captured or loaded onto a top bobbin. The total denier of the suture stock was 3040. The knot pull was 23.5 kg (average of several tests). The break load was 41.3 kg (average of several tests) and the break load % was 29.4 (average of several tests). The average diameter was 0.761, which corresponds to USP size 5.

All publications and patents cited herein are incorporated herein by reference in their entirety for the purpose of describing and disclosing, for example, materials and methodologies described in the publications, which might be used in connection with the presently described invention. The publications discussed above and throughout the text are provided solely for their disclosure prior to the filing date of the present application. Nothing herein is to be construed as an admission that the inventors are not entitled to antedate any referenced publication by virtue of prior invention.

Any of the various embodiments described above can be combined to provide further embodiments. Aspects of the embodiments can be modified, if necessary to employ concepts of the various patents, applications and publications to provide yet further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:
1. A surgical suture, comprising:
   a) an elongate tubular sleeve surrounding an elongate tubular cavity, the suture lacking a core;
   b) the sleeve comprising a plurality of multifilament strands braided together, the sleeve lacking any monofilament strands;
   c) each of the plurality of multifilament strands comprising a plurality of filaments, some of the plurality of filaments comprising a first polymer chain and some of the plurality of filaments comprising a second polymer chain, the first and second polymer chains being different and the first polymer chain comprising ultra-high molecular polyethylene (UHMWPE);
   d) the plurality of filaments in each of the plurality of the multifilament strands are twisted together, wherein some of the plurality of multifilament strands comprise filaments having the first polymer chain of UHMWPE and other of the plurality of multifilament strands comprise filaments having the second polymer chain, the filaments having the first polymer chain of UHMWPE are twisted at a first twist rate, and the filaments having the second polymer chain are twisted at a second twist rate, the first twist rate and the second twist rate being different from each other; and
   e) the plurality of multifilament strands in the sleeve are braided together.
2. The suture of claim 1 including at least one marker strand.
3. The suture of claim 1 wherein 90% or less of the plurality of multifilament strands in the suture include multifilament strands comprising filaments having the first polymer chain of ultra-high molecular weight polyethylene.
4. The suture of claim 1 wherein 70% or less of the plurality of multifilament strands in the suture include multifilament strands comprising filaments having the first polymer chain of ultra-high molecular weight polyethylene.
5. The suture of claim 1 wherein the second polymer chain is nylon.
6. The surgical suture of claim 5, wherein the first twist rate is 200 turns per meter, and the second twist rate is 300 turns per meter.
7. The suture of claim 1 wherein the plurality of multifilament strands includes 11 strands of UHMWPE and 5 strands of nylon and is a USP size 2 suture.
8. A surgical suture, comprising:
   a) an elongate tubular sleeve surrounding an elongate tubular cavity, the suture lacking a core;
   b) the sleeve comprising of a plurality of multifilament strands braided together, the sleeve lacking any monofilament strands;

c) each of some of the plurality of multifilament strands comprising a plurality of filaments consisting of a plurality of UHMWPE filaments, and each of some of the plurality of multifilament strands comprising of a plurality of filaments consisting of nylon filaments, wherein each UHMWPE filament of the plurality of UHMWPE filaments comprises a plurality of polymer chains that are ultra-high molecular polyethylene (UHMWPE), and wherein each nylon filament of the plurality of nylon filaments comprises a plurality of polymer chains that are nylon;

d) the plurality of filaments in each of the multifilament strands are twisted together, wherein the filaments having the polymer chain of UHMWPE are twisted at a first twist rate of 200 turns per meter, and the filaments having the polymer chain of nylon are twisted at a second twist rate of 300 turns per meter;

e) the plurality of multifilament strands in the sleeve are braided together at 17 or 14.5 plaits per centimeter; and f) the suture are USP size 2.

9. A method of making a surgical suture stock which can be cut to form surgical suture, the surgical suture stock comprising an elongate tubular sleeve surrounding an elongate tubular cavity, the surgical suture stock lacking a core, the method comprising braiding together a plurality of multifilament strands at 14.5 or 17 plaits per centimeter to form a sleeve, the sleeve lacking any monofilament strands, wherein:

the plurality of multifilament strands consist of some multifilament strands having a plurality of ultra-high molecular polyethylene (UHMWPE) filaments and other multifilament strands having a plurality of nylon filaments;

the plurality of UHMWPE filaments comprises a plurality of polymer chains that are (UHMWPE);

the plurality of nylon filaments comprises a plurality of polymer chains that are nylon; and the plurality of UHMWPE filaments and the plurality of nylon filaments in each of the multifilament strands are twisted together at 200 or 300 turns per meter, wherein the plurality of multifilament strands comprising UHMWPE having the polymer chains that are UHMWPE are twisted at a first twist rate of 200 turns per meter, and the plurality of multifilament strands comprising the nylon filaments having the polymer chains of nylon are twisted at a second twist rate of 300 turns per meter.

* * * * *

UNITED STATES PATENT AND TRADEMARK OFFICE
CERTIFICATE OF CORRECTION

PATENT NO. : 11,166,714 B2
APPLICATION NO. : 15/523846
DATED : November 9, 2021
INVENTOR(S) : Brian S. Hallett It is certified that error appears in the above-identified patent and that said Letters Patent is hereby corrected as shown below:

In the Claims

<u>Column 18, Line 11, Claim 9:</u>
"(UHMWPE)" should read: --UHMWPE--.

Signed and Sealed this
Twenty-eighth Day of February, 2023

Katherine Kelly Vidal
*Director of the United States Patent and Trademark Office*